United States Patent [19]

Siegle et al.

[11] 4,113,876

[45] Sep. 12, 1978

[54] SULFONIC ACID-N-METHYLAMIDO-N-SULFENYL-N-METHYL-CARBAMIC ACID ESTERS

[75] Inventors: Peter Siegle, Cologne; Engelbert Kühle, Bergisch-Gladbach; Ingeborg Hammann, Cologne; Bernhard Homeyer, Opladen; Wolfgang Behrenz, Overath-Steinebrueck, all of Germany

[73] Assignee: Bayer Aktiengesellschaft, Leverkusen, Germany

[21] Appl. No.: 592,860

[22] Filed: Jul. 2, 1975

[30] Foreign Application Priority Data

Jul. 16, 1974 [DE] Fed. Rep. of Germany ....... 2434184

[51] Int. Cl.$^2$ .................. A01N 9/16; C07D 307/86; C07D 317/28
[52] U.S. Cl. .................. 424/278; 424/282; 424/285; 424/300; 260/340.5 R; 260/340.7; 260/340.9 R; 260/346.73; 260/465 D; 260/465 A; 560/10; 560/13; 560/134; 560/135; 560/136; 560/137
[58] Field of Search .......... 260/346.2 R, 340.5, 260/340.7, 340.9, 465 D, 465 H; 424/285, 282, 278, 300; 560/10, 13, 134, 135, 136, 137

[56] References Cited

U.S. PATENT DOCUMENTS 3,954,836  5/1976  Siegle et al. ................. 260/340.5

FOREIGN PATENT DOCUMENTS

| 674,792 | 0000 | Belgium. |
| 2,254,359 | 5/1974 | Fed. Rep. of Germany. |
| 1,138,277 | 10/1962 | Fed. Rep. of Germany. |
| 1,145,162 | 3/1963 | Fed. Rep. of Germany. |

Primary Examiner—Henry R. Jiles
Assistant Examiner—Bernard Dentz

Attorney, Agent, or Firm—Burgess, Dinklage & Sprung

[57] ABSTRACT

Sulfonic acid-N'-methylamido-N'-sulfenyl-N-methyl-carbamic acid esters of the formula

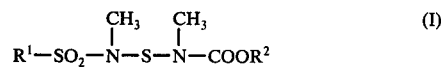

in which
R$^1$ is dialkylamino with 1-4 carbon atoms in each alkyl group, phenyl substituted in the o- or m-position by halogen or by alkyl with 1-4 carbon atoms, or phenyl substituted in the o-, m- or p-position by NO$_2$, CF$_3$ or CN, and R$^2$ is phenyl, naphthyl, benzodioxolanyl or indanyl; phenyl, naphthyl, benzodioxolanyl or indanyl substituted by trihalogenomethyl, halogen, nitro, cyano, formamidino, dioxanyl or dioxolanyl, or by alkyl, alkenyl, alkynyl, alkoxy, alkenoxy, alkynoxy, alkylmercapto, alkenylmercapto or dialkylamino wherein each hydrocarbon portion has 1-4 carbon atoms; cycloalkyl of 5-7 carbon atoms, or

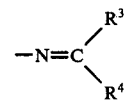

in which
R$^3$ and R$^4$ each independently is cyano or alkyl, alkoxy, alkylthio or alkoxycarbonyl with 1-4 carbon atoms in each alkyl group, or R$^3$ and R$^4$ together form a ring, or, provided that R$^1$ is a NO$_2$-substituted phenyl, R$^2$ may be dihydrobenzofuranyl or dihydrobenzofuranyl substituted by alkyl of 1-4 cabon atoms, which possess insecticidal, acaricidal, nematicidal, fungicidal and herbicidal properties.

7 Claims, No Drawings

SULFONIC ACID-N-METHYLAMIDO-N-SULFENYL-N-METHYL-CARBAMIC ACID ESTERS

The present invention relates to and has for its objects the provision of particular new sulfonic acid-N'-methylamide-N'-sulfenyl-N-methyl-carbamic acid esters, i.e., dialkylamino-, phenyl- or substituted phenyl-sulfonic acid-N'-methylamino-N'-sulfenyl-N-methyl-carbamic acid esters. of phenols, naphthols, benzodioxolanols, indanols or hydroximines, which possess insecticidal, acaricidal, nematicidal, fungicidal and herbicidal properties, active compositions in the form of mixtures of such compounds with solid and liquid dispersible carrier vehicles, and methods for producing such compounds and for using such compounds in a new way especially for combating pests, e.g., insects, acarids, nematodes and fungi, and unwanted vegetation, with other and further objects becoming apparent from a study of the within specification and accompanying examples.

It has been disclosed in German Published Specification DAS Nos. 1,145,162 and 1,138,277 and Belgian Pat. No. 674,792 that carbamates are active insecticides. Some of the compounds described there are commercially available products but have the disadvantage that they are not always entirely satisfactory, especially when used at low concentrations.

The present invention provides, as new compounds, the N-sulfenylated carbamates of the general formula

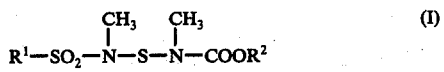

$$R^1-SO_2-N(CH_3)-S-N(CH_3)-COOR^2 \quad (I)$$

in which
$R^1$ is dialkylamino with 1–4 carbon atoms in each alkyl group, phenyl substituted in the o- or m-position by halogen or by alkyl with 1–4 carbon atoms, or phenyl substituted in the o-, m- or p-position by $NO_2$, $CF_3$ or CN, and
$R^2$ is phenyl, naphthyl, benzodioxolanyl or indanyl, phenyl, naphthyl, benzodioxolanyl or indanyl substituted by trihalogenomethyl, halogen, nitro, cyano, formamidino, dioxanyl or dioxolanyl or by alkyl, alkenyl, alkynyl, alkoxy, alkenoxy, alkynoxy, alkylmercapto, alkenylmercapto, alkynylmercapto or dialkylamino wherein each hydrocarbon portion has 1–4 carbon atoms; cycloalkyl of 5–7 carbon atoms, or

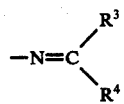

$$-N=C\begin{smallmatrix}R^3\\R^4\end{smallmatrix}$$

in which
$R^3$ and $R^4$ each independently is cyano, or alkyl, alkoxy, alkylthio or alkoxycarbonyl with 1–4 carbon atoms in each alkyl group, or $R^3$ and $R^4$ together form a ring, or, provided that $R^1$ is a $NO_2$-substituted phenyl, $R^2$ may be dihydrobenzofuranyl or dihydrobenzofuranyl substituted by alkyl of 1–4 carbon atoms.

Preferably, $R^1$ is dimethylamino, 2-chlorophenyl, 3-chlorophenyl, 2-nitrophenyl, 3-nitrophenyl, 4-nitrophenyl, 3-trifluoromethylphenyl, 2-tolyl or 3-tolyl, and $R^2$ is phenyl, 2-isopropoxyphenyl, 3,5-dimethyl-4-methylmercapto-phenyl, 3-methyl-4-dimethylaminophenyl, 4-nitrophenyl, 2-allyloxyphenyl, 3isopropylphenyl, 3-sec.-butyl-4-methylphenyl, 4-methyl-3-isopropylphenyl, 2-dimethylaminophenyl, 1-naphthyl, 4-(1,1-dimethylindanyl), 2,2-dimethylbenzodioxolanyl, 2-dioxolan-(1',3')-yl-(2')-phenyl, 2,4-dinitro-6-sec.-butyl-phenyl or 2,2-dimethyl-2,3-dihydrobenzofuranyl-(7) or a radical derived from acetonoxime, dichloroacetonoxime, malonic acid diethyl ester oxime, 2-oximino-1,3-dithiolane, 4-methyl-2-oximino-1,3-dithiolane, 4,4-dimethyl-2-oximino-1,3-dithiolane, 4-phenyl-2-oximino-1,3-dithiolane, 2-oximino-1,3-oxathiolane, 2-oximino-1,3-dithiane, 2-oximino-1,3-oxathiane, the methylthio ester of hydroxamacetic acid or the n-butylthio ester of hydroxamacetic acid.

It is distinctly surprising that the compounds according to the invention show a greater insecticidal, acaricidal and nematicidal action than the known commercially available carbamates of the same type of action. Furthermore, the sulfenylated carbamates according to the invention are less toxic than the non-sulfenylated carbamates on which they are based. Accordingly, they represent an enrichment of the art.

The present invention also provides a process for the preparation of an N-sulfenylated carbamate of the formula (I) in which a carbamic acid fluoride of the general formula

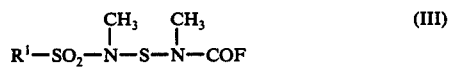

$$R^1-SO_2-N(CH_3)-S-N(CH_3)-COF \quad (III)$$

in which
$R^1$ has the above-mentioned meaning, is reacted with the compound of the general formula $$R^2-OH \quad (IV),$$

in which
$R^2$ has the above-mentioned meaning, if appropriate in the presence of an acid-binding agent and of a diluent.

If N-methyl-(3-trifluoromethylbenzenesulfonic acid methylamide-N'-sulfenyl)-carbamic acid fluoride and α-methylthio-acetaldoxime are used as starting materials, of course of the reaction can be represented by the following equation:

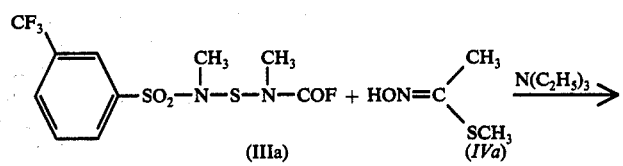

-continued

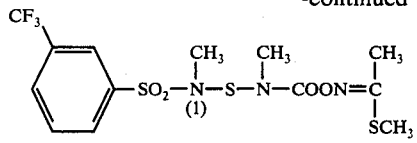

The phenols and oximes of the general formula (IV) which are employed as starting materials are known.

Substituted carbamic acid fluorides (III) which are employed as starting materials are described in German published Specification DOS No. 2,311,284. As described there, they can be prepared by reacting benzenesulfonic acid methylamides with disulfur dichloride, followed by reaction of the resulting disulfide with chlorine to give the corresponding sulfenyl chloride. The sulfenyl chlorides thus obtained are then reacted with N-methylcarbamic acid fluoride to give the carbamic acid fluorides of the formula (III).

All inert organic solvents can be used as diluents when carrying out the preparative process according to this invention. These include ethers, such as diethyl ether, tetrahydrofuran and dioxane, hydrocarbons, such as benzene, and chlorohydrocarbons, such as chloroform and chlorobenzene.

To bind the hydrogen fluoride produced in the reaction, a tertiary organic base such as, for example, triethylamine is preferably added to the reaction mixture.

The reaction temperatures can be varied within a fairly wide range. In general, the reaction is carried out at between 0° and 100° C, preferably at from 20° to 40° C.

In carrying out the process according to the invention, equimolar amounts are preferably used; the use of an excess of one or other starting material does not result in a significant increase in yield.

The active compounds according to the invention couple a low toxicity to warm-blooded animals with powerful insecticidal, acaricidal and nematicidal properties and can therefore be employed with good success for combating harmful sucking and biting insects, as well as against pests harmful to health and pests of stored products, mites, soil insects and nematodes.

In addition, the compounds according to the invention also possess certain fungicidal and herbicidal properties.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*) the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*) the ermine moth (*Hyponomeuta padella*), the mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneium*), the northern corn billbug (Calendra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (Leucopheae or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such s the vinegar fly (*Drosophila melanogaster*), the Mediterranean fruit fly (*Ceratitus capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (*Tetranychidae*) such as the two-spotted spider mite (*Tetranychus urticae*) and the European red mite (*paratetranychus pilosus* = *Panonychus ulmi*), gall mites, for example the blackcurrent gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present products are also distinguished by an outstanding residual activity on wood and clay, as well as a good stability to alkali on limed substrates.

The active compounds according to the invention couple a low toxicity to warm-blooded animals with powerful nematicidal properties and can therefore be used to combat nematodes, especially phytophathogenic nematodes. These essentially include leaf nematodes (Arphelenchoides), such as the chrysanthemum eelworm (*A. ritzemabosi*), the leaf-bloth eelworm (*A. fragariae*) and the rice eelworm (*A. orzyae*); stem nematodes (Ditylenchus), such as the stem eelworm (*D. Dipsaci*); root-knot nematodes (Meloldogyne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes,etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketones, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfontes, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematicides, fungicides and herbicides, or bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g., insects, acarids, nematodes and fungi and unwanted vegetation, and more particularly methods of combating insects, acarids and nematodes, which comprises applying to at least one of the correspondingly (a) such insects, (b) such acarids, (c) such nematodes, (d) such fungi, (e) such unwanted vegetation and (f) the corresponding habitat thereof, i.e., the locus to be protected, e.g., to a growing crop, to an area where a crop is to be grown or to a domestic animal, a correspondingly combative or toxic amount, i.e., insecticidally, acaricidally, nematicidally, fungicidally or herbicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

*Phaedon* larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all the beetle larvae had been killed whereas 0% means that none of the beetle larvae had been killed.

The active compounds, the concentrations of the active compounds, the evaluation times and the results can be seen from the following table.

TABLE 1

(insects which damage plants)
*Phaedon* larvae test

| Active compounds | Active Compound Concentration in % | Degree of destruction in % after 3 days |
|---|---|---|
| (A) CH₃—S—C(CH₃)=N—OCO—NHCH₃ (known) | 0.1<br>0.01 | 100<br>0 |
| (6) (CH₃)₂N—SO₂—N(CH₃)—S—N(CH₃)—COON=C(S—CH₂—CH₂—S) | 0.1<br>0.01 | 100<br>100 |
| (7) (CH₃)₂N—SO₂—N(CH₃)—S—N(CH₃)—COO—C₆H₄—C₃H₇(i) | 0.1<br>0.01 | 100<br>100 |
| (8) (CH₃)₂N—SO₂—N(CH₃)—S—N(CH₃)—COO—C₆H₄-(1,3-dioxolan-2-yl) | 0.1 | 95 |
| (10) (CH₃)₂N—SO₂—N(CH₃)—S—N(CH₃)—COO—C₆H₃(CH₃)(N(CH₃)₂) | 0.1<br>0.01 | 100<br>100 |
| (2) CF₃—C₆H₄—SO₂—N(CH₃)—S—N(CH₃)—COO—C₆H₄—C₃H₇(i) | 0.1<br>0.01 | 100<br>100 |
| (3) CF₃—C₆H₄—SO₂—N(CH₃)—S—N(CH₃)—COO—C₆H₄-(1,3-dioxolan-2-yl) | 0.1<br>0.01 | 100<br>100 |
| (11) NO₂—C₆H₄—SO₂—N(CH₃)—S—N(CH₃)—COO—N=C(CN)—C(CH₃)₂—CH₃ | 0.01 | 100 |

TABLE 1-continued (insects which damage plants)
*Phaedon* larvae test

| Active compounds | Active Compound Concentration in % | Degree of destruction in % after 3 days |
|---|---|---|
| (12) 2-NO$_2$-C$_6$H$_4$-SO$_2$-N(CH$_3$)-S-N(CH$_3$)-COO-(2,3-dihydro-2,2-dimethylbenzofuran-7-yl) | 0.01 | 100 |
| (13) 2-NO$_2$-C$_6$H$_4$-SO$_2$-N(CH$_3$)-S-N(CH$_3$)-COO-N=C(CN)-C(CH$_3$)$_3$ | 0.01 | 100 |
| (17) 3-Cl-C$_6$H$_4$-SO$_2$-N(CH$_3$)-S-N(CH$_3$)-COON=C(CN)-C(CH$_3$)$_2$ | 0.01 | 100 |

EXAMPLE 2

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleacea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

TABLE 2

(insects which damage plants)
*Myzus* test

| Active Compounds | Active Compound Concentration in % | Degree of destruction in % after 1 day |
|---|---|---|
| (B) (CH$_3$)$_2$N-C$_6$H$_3$(3-CH$_3$)-O-C(=O)-NHCH$_3$ (known) | 0.1<br>0.01 | 98<br>20 |
| (6) (CH$_3$)$_2$N-SO$_2$-N(CH$_3$)-S-N(CH$_3$)-COON=C(1,3-dithiolan-2-ylidene) | 0.1<br>0.01 | 100<br>95 |
| (1) 3-CF$_3$-C$_6$H$_4$-SO$_2$-N(CH$_3$)-S-N(CH$_3$)-COON=C(CH$_3$)(SCH$_3$) | 0.1<br>0.01 | 100<br>100 |
| (11) 3-NO$_2$-C$_6$H$_4$-SO$_2$-N(CH$_3$)-S-N(CH$_3$)-COO-N=C(CN)-C(CH$_3$)$_3$ | 0.01 | 100 |

TABLE 2-continued (insects which damage plants)
Myzus test

| Active Compounds | Active Compound Concentration in % | Degree of destruction in % after 1 day |
|---|---|---|
| (12) 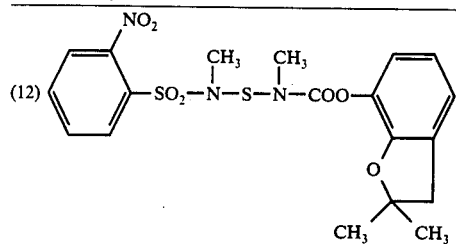 | 0.01 | 100 |
| (13) 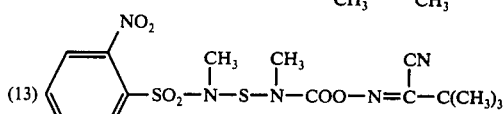 | 0.01 | 100 |
| (14) 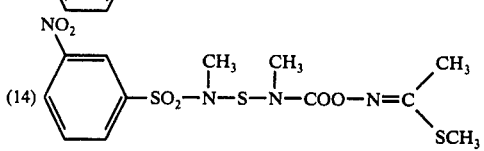 | 0.1<br>0.01 | 100<br>99 |
| (15) 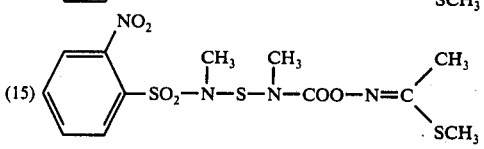 | 0.1<br>0.01 | 100<br>99 |

EXAMPLE 3

*Doralis* test (systemic action)

Solvent: 3 parts by weight dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following table:

TABLE 3

(insects which damage plants)
Doralis test (systemic action)

| Active Compounds | Active Compound concentration in % | Degree of destruction in % after 4 days |
|---|---|---|
| (B) 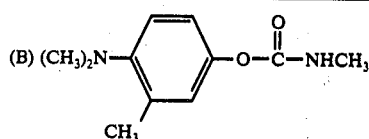<br>(known) | 0.1<br>0.01 | 100<br>0 |
| (5) 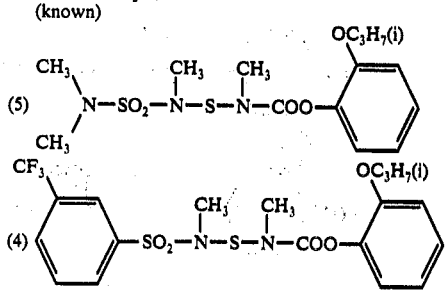 | 0.1<br>0.01 | 100<br>100 |
| (4) | 0.1<br>0.01 | 100<br>100 |

TABLE 3-continued (insects which damage plants)
Doralis test (systemic action)

| Active Compounds | Active Compound concentration in % | Degree of destruction in % after 4 days |
| --- | --- | --- |
| (1) 3-CF$_3$-C$_6$H$_4$-SO$_2$-N(CH$_3$)-S-N(CH$_3$)-COON=C(CH$_3$)(SCH$_3$) | 0.1<br>0.01 | 100<br>100 |
| (11) 3-NO$_2$-C$_6$H$_4$-SO$_2$-N(CH$_3$)-S-N(CH$_3$)-COO-N=C(CN)-C(CH$_3$)$_3$ | 0.01 | 100 |
| (12) 2-NO$_2$-C$_6$H$_4$-SO$_2$-N(CH$_3$)-S-N(CH$_3$)-COO-(2,2-dimethyl-2,3-dihydrobenzofuran-7-yl) | 0.01 | 100 |
| (13) 2-NO$_2$-C$_6$H$_4$-SO$_2$-N(CH$_3$)-S-N(CH$_3$)-COO-N=C(CN)-C(CH$_3$)$_3$ | 0.01 | 100 |
| (14) 3-NO$_2$-C$_6$H$_4$-SO$_2$-N(CH$_3$)-S-N(CH$_3$)-COO-N=C(CH$_3$)(SCH$_3$) | 0.01 | 100 |
| (15) 2-NO$_2$-C$_6$H$_4$-SO$_2$-N(CH$_3$)-S-N(CH$_3$)-COO-N=C(CH$_3$)(SCH$_3$) | 0.01 | 100 |
| (16) 3-Cl-C$_6$H$_4$-SO$_2$-N(CH$_3$)-S-N(CH$_3$)-COON=C(CH$_3$)(SCH$_3$) | 0.01 | 100 |

EXAMPLE 4

*Tetranychus* test (resistant)

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

TABLE 4

| Active compounds | Active compound concentration in % | Degree of destruction in % after 2 days |
|---|---|---|
| (C) (known) 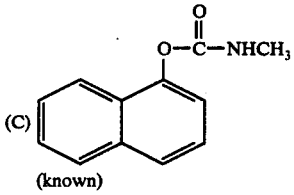 | 0.1 | 0 |
| (9) 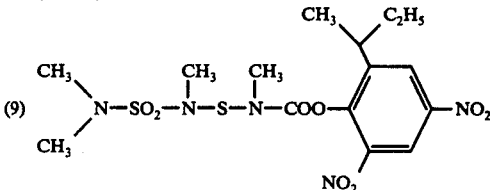 | 0.1 | 100 |
| (1) 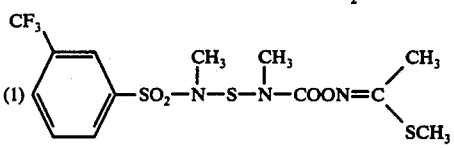 | 0.1 | 90 |
| (11) 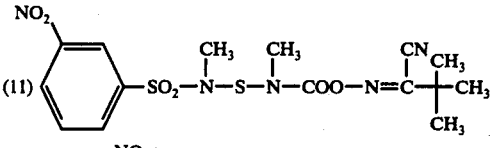 | 0.1 | 100 |
| (13) 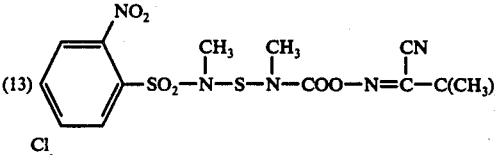 | 0.1 | 100 |
| (17) 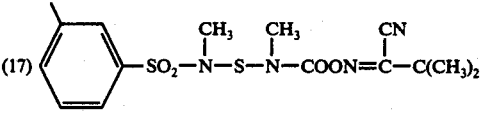 | 0.1 | 98 |

EXAMPLE 5

Critical concentration test/soil insects
  Test insect: *Phorbia antiqua* - grubs
  Solvent: 3 parts by weight of acetone
  Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which was quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 5

Soil insecticides
*Phorbia antiqua* - grubs in the soil

| Active compound | Degree of destruction in % (active compound concentration = 10 ppm) |
|---|---|
| (B) 4-(dimethylamino)-3-methylphenyl N-methylcarbamate (known) | 0 |
| (C) 1-naphthyl N-methylcarbamate (known) | 0 |
| (5) (CH$_3$)$_2$N—SO$_2$—N(CH$_3$)—S—N(CH$_3$)—COO—[2-(i-C$_3$H$_7$O)phenyl] | 100 |
| (4) [3-CF$_3$-phenyl]—SO$_2$—N(CH$_3$)—S—N(CH$_3$)—COO—[2-(i-C$_3$H$_7$O)phenyl] | 100 |
| (3) [3-CF$_3$-phenyl]—SO$_2$—N(CH$_3$)—S—N(CH$_3$)—COO—[2-(1,3-dioxolan-2-yl)phenyl] | 100 |
| (11) [3-NO$_2$-phenyl]—SO$_2$—N(CH$_3$)—S—N(CH$_3$)—COO—N=C(CN)—C(CH$_3$)$_3$ | 100 |
| (12) [2-NO$_2$-phenyl]—SO$_2$—N(CH$_3$)—S—N(CH$_3$)—COO—[2,2-dimethyl-2,3-dihydrobenzofuran-7-yl] | 100 |
| (13) [2-NO$_2$-phenyl]—SO$_2$—N(CH$_3$)—S—N(CH$_3$)—COO—N=C(CN)—C(CH$_3$)$_3$ | 100 |

EXAMPLE 6

Critical concentration test
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compound, the amounts applied and the results can be seen from the following table:

emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which was quoted in ppm (= mg/1). The soil was filled into pots and the pots were left to stand at room temperature.

Table 6

Nematicides/*Meloidogyne incognita*

| Active compound | Degree of destruction in % (active compound concentration in ppm: 10) |
|---|---|
| (B) $(CH_3)_2N-\text{[phenyl, }CH_3\text{]}-O-\overset{O}{\underset{\parallel}{C}}-NHCH_3$ (known) | 0 |
| (C) $\text{[naphthyl]}-O-\overset{O}{\underset{\parallel}{C}}-NH-CH_3$ (known) | 0 |
| (6) $\overset{CH_3}{\underset{CH_3}{N}}-SO_2-\overset{CH_3}{\underset{\vert}{N}}-S-\overset{CH_3}{\underset{\vert}{N}}-COON=C\overset{S-}{\underset{S-}{\diagdown}}$ | 100 |
| (1) $CF_3-\text{[phenyl]}-SO_2-\overset{CH_3}{\underset{\vert}{N}}-S-\overset{CH_3}{\underset{\vert}{N}}-COON=C\overset{CH_3}{\underset{SCH_3}{\diagdown}}$ | 100 |

EXAMPLE 7

Critical concentration test/soil insects

Test insect: *Tenebrio molitor* larvae

Solvent: 3 parts by weight of acetone

Emulsifier: 1 part by weight of alkylaryl polyglycol ether

To produce a suitable preparation of active compound, 1 part by weight of active compound was mixed with the stated amount of solvent, the stated amount of After 24 hours the test insects were introduced into the treated soil and after a further 2 to 7 days the degree of effectiveness of the active compound was determined in % by counting the dead and live test insects. The degree of effectiveness is 100% if all the test insects had been killed and is 0% if exactly as many test insects were still alive as in the case of the untreated control.

The active compounds, amounts used and results can be seen from the table which follows:

Table 7

Soil insecticides
*Tenebrio molitor* larvae in the soil

| Active compound | Degree of destruction in % at an active compound concentration of 10 ppm |
|---|---|
| (B) $(CH_3)_2N-\text{[phenyl, }CH_3\text{]}-O-\overset{O}{\underset{\parallel}{\text{N}}}HCH_3$ (known) | 0 |

Table 7-continued
Soil insecticides
*Tenebrio molitor* larvae in the soil

| Active compound | Degree of destruction in % at an active compound concentration of 10 ppm |
|---|---|
| (C) naphthyl-O-C(=O)-NH-CH₃ (known) | 0 |
| (21) 3-Cl-C₆H₄-SO₂-N(CH₃)-S-N(CH₃)-COON=C(CH₃)₂ | 100 |

The process of the invention is further illustrated by the following preparative example.

EXAMPLE 8

(a) (i) Preparation of bis-(3-chlorobenzenesulfonic acid methylamido)-disulfide 20.5 g (0.1 mole) of 3-chlorobenzenesulfonic acid methylamide were suspended in 100 ml of carbon tetrachloride and 11 g of triethylamine were added. 6.75 g (0.05 mole) of disulfur dichloride were then slowly added dropwise at room temperature, while stirring. In the course thereof, the temperature did not rise above 25° C. The mixture was stirred for a further 4 hours at room temperature. The product was then filtered off, washed twice with dilute cold NaOH, dried and concentrated. The residue was recrystallized from chloroform and petroleum ether. Melting point 103° C; yield 19 g.

The following were prepared analogously:

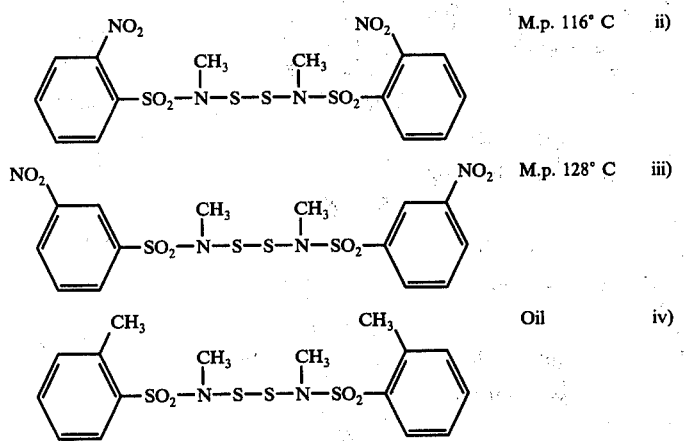

stirred for a further hour at room temperature. After concentration, a viscous oil remained; this was digested with ether. Melting point 72° C; yield 55 g.

The following were prepared analogously:

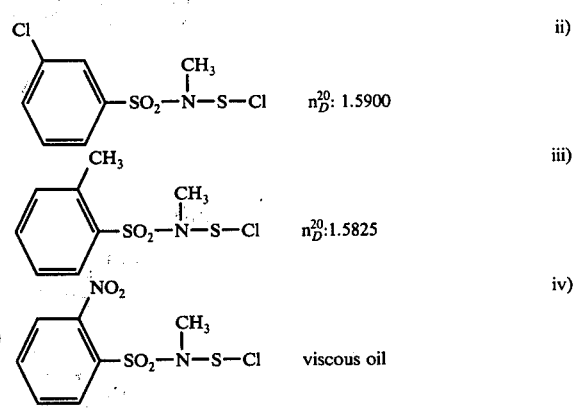

(b) (i) Preparation of (3-nitrobenzenesulfonic acid-methylamido)-sulfenyl chloride 52.5 g (0.1 mole) of bis-(3-nitrobenzenesulfonic acid-methylamido)-disulfide prepared as in(a) (iii) were suspended in 150 ml of absolute carbon tetrachloride. Chlorine was then passed in at 15°–20° C until a clear reddish solution had been produced. The mixture was (c) (i) Preparation of (2-nitrobenzenesulfonic acid-N'-methylamido-N'-sulfenyl)-N-methyl-carbamic acid-fluoride 70.6 g (0.25 mole) of (2-nitrobenzenesulfonic acid methylamido)-sulfenyl chloride were dissolved in 400 ml of absolute toluene and 19.2 g (0.25 mole) of N-methyl-carbamic acid fluoride were added. 27 g of triethylamine were slowly added dropwise while stirring and cooling. The mixture was stirred for a further 2 hours at 40° C, the product was filtered off and the solvent was evaporated off. The product was digested with ether. Melting point 114° C; yield 68 g. The following were prepared analogously

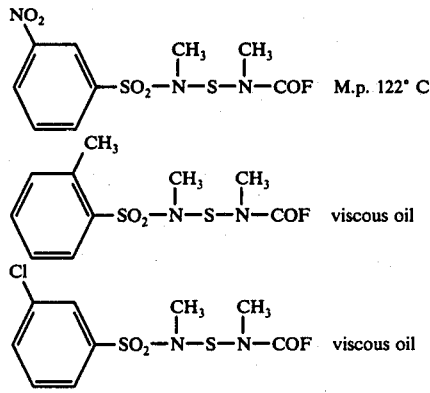

d) 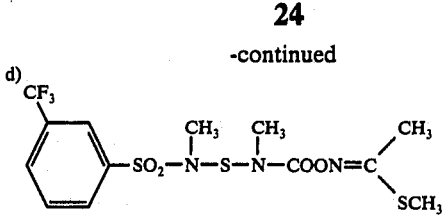 (1)

17.3 g (0.05 mole) of (3-trifluoromethyl-benzenesulfonic acid-N'-methylamido-N'-sulfenyl)-N-methylcarbamic acid fluoride, produced as in (a), (b), and (c), and 5.3 g (0.05 mole) of α-methylthioacetaldoxime were suspended in 150 ml of absolute toluene. 6 g of trimethylamine were added dropwise at room temperature, while stirring. The mixture was stirred for a further 2 hours at 30° C. It was then washed repeatedly with cold water and the organic phase was dried and concentrated. An oily residue remained. Yield 17 g; $n_D^{25}$ = 1.5310.

The following were prepared analogously:

| Compound | Formula | Physical properties |
|---|---|---|
| (2) | 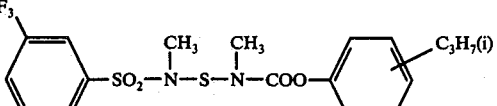 Mixture of the m- and p-substituted compounds in the ratio of 60:40 | $n_D^{25}$: 1.5261 |
| (3) | 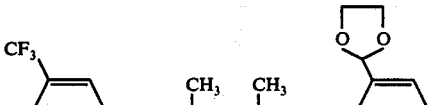 | $n_D^{25}$: 1.5331 |
| (4) | 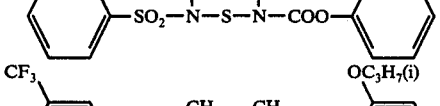 | $n_D^{25}$: 1.5222 |
| (5) | 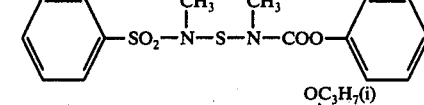 | viscous oil |
| (6) | 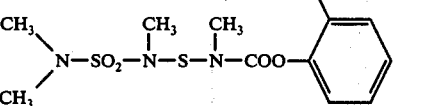 | M.p. 132° C |
| (7) | 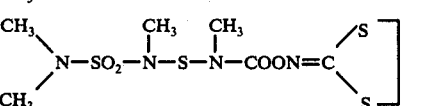 Mixture of the m- and p-substituted compounds in the ratio of 60:40 | $n_D^{25}$: 1.5242 |
| (8) | 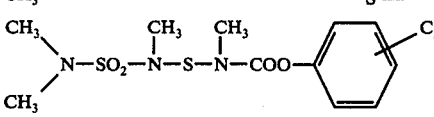 | $n_D^{25}$: 1.517 |

-continued

| Compound | Formula | Physical properties |
|---|---|---|
| (9) | (CH₃)₂N—SO₂—N(CH₃)—S—N(CH₃)—COO—[2,4-dinitro-6-(CH(C₂H₅)CH₃)phenyl] | $n_D^{25}$: 1.535 |
| (10) | (CH₃)₂N—SO₂—N(CH₃)—S—N(CH₃)—COO—[4-(N(CH₃)₂)-3-methylphenyl] | $n_D^{25}$: 1.541 |
| (11) | 3-NO₂-C₆H₄—SO₂—N(CH₃)—S—N(CH₃)—COO—N=C(CN)—C(CH₃)₃ | viscous oil |
| (12) | 2-NO₂-C₆H₄—SO₂—N(CH₃)—S—N(CH₃)—COO—[2,2-dimethyl-2,3-dihydrobenzofuran-7-yl] | viscous oil |
| (13) | 2-NO₂-C₆H₄—SO₂—N(CH₃)—S—N(CH₃)—COO—N=C(CN)—C(CH₃)₃ | M.p. 119° C |
| (14) | 3-NO₂-C₆H₄—SO₂—N(CH₃)—S—N(CH₃)—COO—N=C(CH₃)(SCH₃) | M.p. 115° C |
| (15) | 2-NO₂-C₆H₄—SO₂—N(CH₃)—S—N(CH₃)—COO—N=C(CH₃)(SCH₃) | M.p. 104° C |
| (16) | 3-Cl-C₆H₄—SO₂—N(CH₃)—S—N(CH₃)—COON=C(CH₃)(SCH₃) | viscous oil |
| (17) | 3-Cl-C₆H₄—SO₂—N(CH₃)—S—N(CH₃)—COON=C(CN)—C(CH₃)₂ | M.p. 103° C |
| (18) | 2-CH₃-C₆H₄—SO₂—N(CH₃)—S—N(CH₃)—COO—N=C(CH₃)(SCH₃) | viscous oil |
| (19) | 2-CH₃-C₆H₄—SO₂—N(CH₃)—S—N(CH₃)—COO—N=C(CN)—C(CH₃)₃ | $n_D^{25}$: 1.5362 |

-continued

| Compound | Formula | Physical properties |
|---|---|---|
| (20) | 3-CF₃-C₆H₄-SO₂-N(CH₃)-S-N(CH₃)-COO-(2,2-dimethyl-1,3-benzodioxol-4-yl) | |

Other compounds which can be similarly prepared include:

(21) 3-Cl-C₆H₄-SO₂-N(CH₃)-S-N(CH₃)-COON=C(CH₃)₂

(22) (C₃H₇)₂N-SO₂-N(CH₃)-S-N(CH₃)-COO-C₆H₄-CH₂-C≡CH (para)

(23) 4-NC-C₆H₄-SO₂-N(CH₃)-S-N(CH₃)-COO-(5-allyl-naphthalen-1-yl)

(24) 3-Cl-C₆H₄-SO₂-N(CH₃)-S-N(CH₃)-COO-(7-allyloxy-2,3-dihydro-1,4-benzodioxin-5-yl)

(25) 3-Cl-C₆H₄-SO₂-N(CH₃)-S-N(CH₃)-COO-(6-propargyloxy-indan-4-yl)

(26) 3-Cl-C₆H₄-SO₂-N(CH₃)-S-N(CH₃)-COO-(6-ethylthio-3,3-dimethyl-indan-4-yl)

(27) 3-CF₃-C₆H₄-SO₂-N(CH₃)-S-N(CH₃)-COO-(7-allylthio-naphthalen-2-yl)

(28) 2-NO₂-C₆H₄-SO₂-N(CH₃)-S-N(CH₃)-COO-C₆H₄-S-CH₂-C≡CH (para)

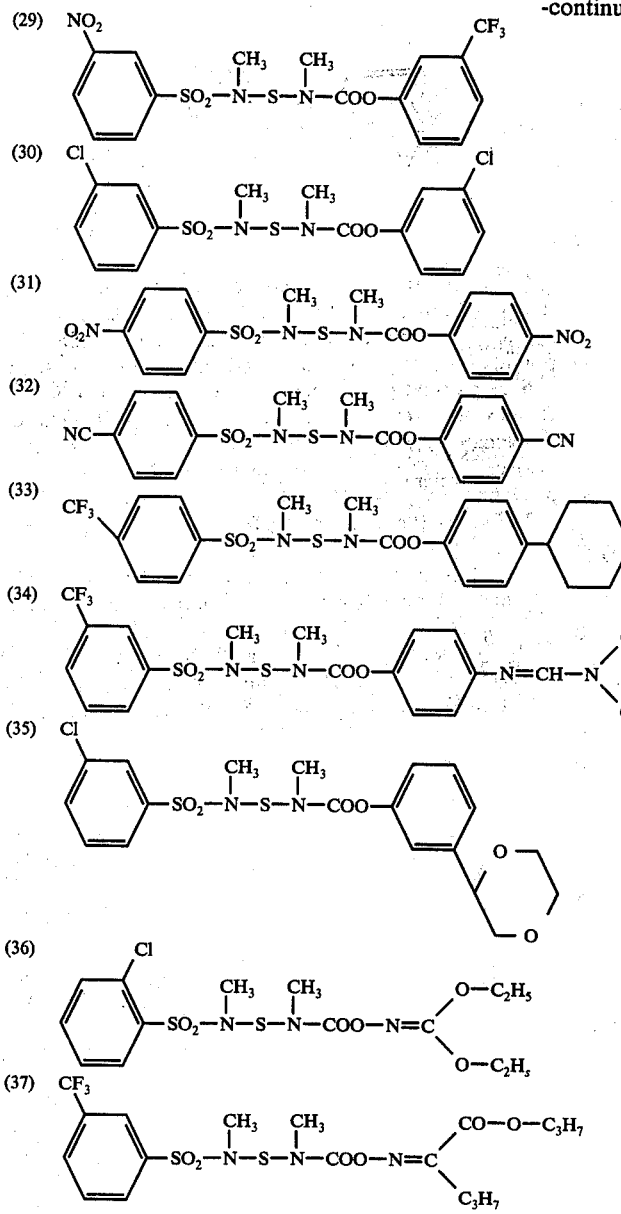

and the like.

It will be appreciated that the instant specification and claims are set forth by way of illustration and not limitation, and that various modifications and changes may be made without departing from the spirit and scope of the present invention.

What is claimed is:

1. A sulfonic acid-N'-methylamido-N'-sulfenyl-N-methyl-carbamic acid ester of the formula

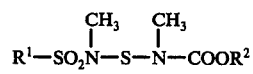

in which $R^1$ is dialkylamino with 1-4 carbon atoms in each alkyl group, or phenyl substituted in the o-, m- or p-position by $NO_2$, $CF_3$ or CN, and $R^2$ is phenyl, naphthyl, benzodioxolanyl or indanyl; phenyl, naphthyl, benzodioxolanyl or indanyl substituted one to three times by trihalogenomethyl, halogen, nitro, cyano, formamidino, dioxanyl or dioxolanyl, or by alkyl, alkenyl, alkynyl, alkoxy, alkenoxy, alkynoxy, alkylmercapto or alkenylmercapto having up to 4 carbon atoms, or by dialkylamino wherein each hydrocarbon portion has 1-4 carbon atoms; cycloalkyl of 5-7 carbon atoms, or, provided that $R^1$ is $NO_2$-substituted phenyl, $R^2$ may be 2,3-dihydrobenzofuranyl-(7) or 2,3-dihydrobenzofuranyl-(7) mono- or di-substituted in 2-position by alkyl of 1-4 carbon atoms.

2. A compound according to claim 1, in which $R^1$ is dimethylamino, 2-nitrophenyl, 4-nitrophenyl, or 3-trifluoromethylphenyl, and $R^2$ is phenyl, 2-isopropoxyphenyl, 3,5-dimethyl-4-methylmercapto-phenyl, 3-methyl-4-dimethylamino-phenyl, 4-nitrophenyl, 2-allyloxyphenyl, 3-isopropylphenyl, 3-sec.-butyl-4-methylphenyl, 4-methyl-3-isopropylphenyl, 2-dimethylaminophenyl, 1-naphthyl, 4-(1,1-dimethylindanyl), 2,2-dimethylbenzodioxolanyl, 2-dioxolan-(1',3')-yl-(2')- phenyl, 2,4-dinitro-6-sec.-butylphenyl or 2,2-dimethyl-2,3-dihydrobenzofuranyl-(7)

3. The compound according to claim 1, in which such compound is (3-trifluoromethyl-benzenesulfonic acid-N′-methylamido-N′-sulfenyl)-N-methyl-carbamic acid ester of 2-(1′,3′-dioxolan(2′)yl)-phenol. of the formula

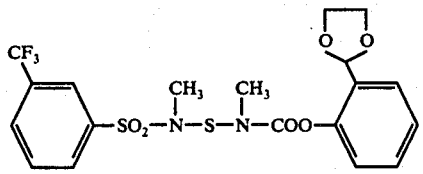

4. The compound according to claim 1, in which such compound is (2-nitro-benzenesulfonic acid-N′-methylamido-N′-sulfenyl)-N-methyl-carbamic acid ester of 2,2-dimethyl-2,3-dihydro-7-hydroxy-benzofuran of the formula

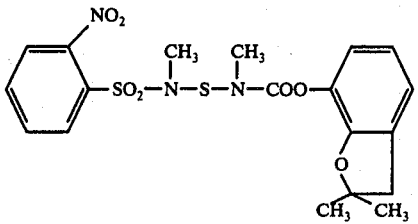

5. An insecticidal, acaricidal or nematicidal composition containing as active ingredient an insecticidally, acaricidally or nematicidally effective amount of a compound according to claim 1 in admixture with a diluent.

6. A method of combating insects, acarids or nematodes which comprises applying to the insects, acarids or nematodes or to a habitate thereof an insecticidally, acaricidally or nematicidally effective amount of a compound according to claim 1.

7. The method according to claim 6 in which said compound is
(3-trifluoromethyl-benzenesulfonic acid -N′-methylamido-N′-sulfenyl)-N-methyl-carbamic acid ester of 2-(1′,3′-dioxolan(2′)yl)-phenol
(2-nitro-benzenesulfonic acid-N′-methylamido-N′-sulfenyl)-N-methyl-carbamic acid ester of 2,2′-dimethyl-2,3-dihydro-7-hydroxy-benzofuran.

* * * * *